United States Patent [19]

Seabrook, Jr. et al.

[11] Patent Number: 5,906,825
[45] Date of Patent: May 25, 1999

[54] POLYMERS CONTAINING ANTIMICROBIAL AGENTS AND METHODS FOR MAKING AND USING SAME

[75] Inventors: Samuel G. Seabrook, Jr., Mount Pleasant; William E. Craver, III, Sullivans Island, both of S.C.

[73] Assignee: Magellan Companies, Inc., Mt. Pleasant, S.C.

[21] Appl. No.: 08/953,908

[22] Filed: Oct. 20, 1997

[51] Int. Cl.$^6$ .................................................. A01N 25/34
[52] U.S. Cl. ........................... 424/404; 424/405; 424/409
[58] Field of Search .................................. 424/404, 405, 424/409

[56] References Cited

U.S. PATENT DOCUMENTS

| | | |
|---|---|---|
| 060,039 | 11/1866 | Needles ................................ 424/195.1 |
| 2,566,410 | 6/1951 | Griffin ................................. 424/195.1 |
| 3,864,468 | 2/1975 | Hyman et al. . |
| 4,086,297 | 4/1978 | Rei et al. . |
| 4,486,450 | 12/1984 | Bernstein . |
| 4,536,404 | 8/1985 | Bernstein . |
| 4,570,038 | 2/1986 | Tinelli . |
| 4,624,679 | 11/1986 | McEntee . |
| 4,661,528 | 4/1987 | Rei . |
| 4,663,077 | 5/1987 | Rei et al. . |
| 4,663,359 | 5/1987 | Rei . |
| 4,666,706 | 5/1987 | Farquharson et al. . |
| 4,666,956 | 5/1987 | Spielau et al. . |
| 4,686,239 | 8/1987 | Rei . |
| 4,747,902 | 5/1988 | Saitoh . |
| 4,761,247 | 8/1988 | Rei et al. . |
| 4,789,692 | 12/1988 | Rei et al. . |
| 4,876,070 | 10/1989 | Tsukahara et al. . |
| 4,888,175 | 12/1989 | Burton, Jr. et al. . |
| 4,891,391 | 1/1990 | McEntee . |
| 4,978,686 | 12/1990 | Sotome ................................... 514/698 |
| 4,981,618 | 1/1991 | Bruneteau et al. . |

(List continued on next page.)

FOREIGN PATENT DOCUMENTS

| | | |
|---|---|---|
| 0144726 | 6/1985 | European Pat. Off. . |
| 1169288 | 11/1969 | United Kingdom . |
| WO9011015 | 10/1990 | WIPO . |

OTHER PUBLICATIONS

Chemical Abstracts, Inoue, Mayumi, Study of Aseptic Packaging of Foods by Using 2–(4–thiazolyl)–benzimidazole in Plastic Film, vol. 89, 1978, p. 470.

Calgon Corporation, Metasol TK–100 Liquid Concentrate, Specialty Chemicals Group.

bio/chem Research Material Safety Data Sheet; Grapefruit Seed Extract.

H&S Chemical Company Material Safety Data Sheet; Trichloromelamine or TCM or N2,N4,N6—Trichloro–2,4, 6–Triamino–1,3,5–Triazine; revised Nov. 29, 1994.

Kalsec Technical Data; Oleoresin Capsicum, Decolorized 2.0% MC; update Sep. 19, 1995.

Kalsec Technical Data; Oleoresin Capsicum, African Type 4.0% MC.

Journal of Agricultural and Food Chemistry, 1991, vol. 39, Nov. 12, 1991; Improved High–Performance Liquid Chromatography Method for the Determination of Major Capsaicinoids in Capsicum Oleoresins; Thomas H. Cooper, James A. Guzinski, and Carolyn Fisher (Kalsec, Inc.).

*Primary Examiner*—Thurman K. Page
*Attorney, Agent, or Firm*—Dority & Manning, P.A.

[57] ABSTRACT

Polymeric compositions containing antimicrobial agents and methods for making and using same are provided. The antimicrobial agents include phytochemicals and phytonutrients such as naturally occurring extracts from plants and herbs and other chemical disinfectants safe for use on food-contact surfaces. Chemical releasers can be added to the compositions for causing the release of the antimicrobial agents. The chemical releasers include citric acid extract. A blend of antimicrobial agents can be included in the composition for destroying and inhibiting the growth of a wide variety of different microorganisms including bacteria, viruses, and fungi.

17 Claims, 3 Drawing Sheets

U.S. PATENT DOCUMENTS

| | | |
|---|---|---|
| 5,063,706 | 11/1991 | Aki et al. . |
| 5,079,600 | 1/1992 | Takamashi et al. .................. 424/195.1 |
| 5,154,748 | 10/1992 | Bruneteau et al. . |
| 5,226,380 | 7/1993 | Fischer . |
| 5,229,124 | 7/1993 | Rei et al. . |
| 5,354,210 | 10/1994 | Koblitz et al. . |
| 5,360,350 | 11/1994 | Koblitz et al. . |
| 5,466,459 | 11/1995 | Wilson ..................... 424/407 |
| 5,500,205 | 3/1996 | Abbott et al. . |
| 5,514,779 | 5/1996 | Broekaert et al. . |
| 5,525,597 | 6/1996 | Hainrihar et al. . |
| 5,554,373 | 9/1996 | Seabrook et al. . |
| 5,639,794 | 6/1997 | Emeron et al. ......................... 514/699 |

POLYMERS CONTAINING ANTIMICROBIAL AGENTS AND METHODS FOR MAKING AND USING SAME

FIELD OF THE INVENTION

This invention relates generally to compositions containing antimicrobial agents and more specifically to polymeric substrates containing antimicrobial agents. In particular, the antimicrobial agents of the present invention are believed to be safe for human contact, in at least one embodiment, safe for contact with food, and in one preferred embodiment, are derived from natural ingredients or from compositions known to be non-toxic.

BACKGROUND OF THE INVENTION

In recent years, polymers and plastics have become increasingly popular and important materials for making various types of articles. These articles, in turn, have been used in a limitless variety of applications. For instance, polymers and plastics are typically used as containers for various articles, such as food items. In some applications, an item contained in a polymeric or plastic article can be subject to attack and contamination by microorganisms. As such, a polymeric or plastic material capable of destroying or inhibiting foreign microorganisms would be highly desirable.

Bacterial contamination of food, especially meat products, has become the focus of growing concern among public health professionals. In 1993, over 500 individuals became ill, and five people died, after eating hamburgers purchased from fast food restaurants. The causative organism, *E. Coli* 0157:H7, is most often associated with ground beef.

Recently, the coccidian parasite Cyclorspora was implicated in an outbreak of gastrointestinal illness among school children, who had ingested contaminated strawberries served for school lunch. Such infection may result in a protracted illness, characterized by frequent, watery stools and other gastrointestinal symptoms; symptoms which may remit and relapse. Although antibiotic therapy is effective to shorten the clinical course associated with Cyclospora infection, no treatment regimen has been identified for patients who cannot tolerate sulfa drugs (MMWR, 46:451, May 23, 1997).

Contamination of foodstuffs by viruses and parasites has recently become of growing concern, because the resulting infections often are refractory to drug treatment. In the majority of persons, the body's immune system is able to limit the replication of such infectious agents, leading to the eventual control and resolution of clinical disease. However, in immunocompromised individuals, such as those suffering from cancer or AIDS, the immune system may not be able to control infection, resulting in a much more serious prognosis.

Although some of the problems associated with microbial contamination of food can be addressed by improved handling and preparation techniques, methods which would reduce contamination during packaging and storage would also significantly decrease the risks associated with food-borne contamination.

A number of methods have been proposed to reduce microbial contamination in foodstuffs prior to preparation. Improvements in poultry processing methods, for example, have reduced the risk of salmonella food poisoning. However, contamination still occurs and any microorganisms present will continue to replicate once the meat is packaged. Thus, special care is still required during storage and handling to prevent food poisoning caused by the ingestion of pathogenic microbes.

During packaging, the treatment of foodstuffs with agents capable of reducing or eliminating microorganisms would decrease the risks associated with food-borne illnesses. However, most of these agents are themselves associated with unacceptable safety risks.

For example, irradiating fruit and milk has been shown to reduce microbial contamination, but safety concerns have prevented the wide-spread acceptance of irradiated products.

The use of antimicrobials could also effectively reduce contamination associated with foodstuffs. However, because the use of such drugs has been associated with the development of resistant organisms, such an approach is currently impractical.

However, many naturally occurring plants and herbs have been shown to possess antimicrobial activity and their use has been shown to be safe for human and animal consumption. Extracts of such plants and herbs, known as phytochemicals or phytonutrients, may be useful to reduce microbial contamination during the processing and storage of foodstuffs, while providing the added advantage of being safe for contact with consumables.

The present invention is concerned with reducing microbial contamination of organic materials, including but not limited to the processing and storage of foodstuffs. Other uses include treating bio-fouling problems associated with the production of a biofilm on marine and industrial equipment. Currently the treatment of bio-fouling includes the use of toxic chemicals, thus creating waste problems with bio-hazardous material. In general terms, the present invention relates to the incorporation of antimicrobial agents into polymeric materials, such that the activity of the agents will reduce the microbial contamination of the organic material with which it comes in contact. In a particular application for plastic food wrappers, antimicrobial agents are mixed with polymer compositions during formation of the plastic sheeting and molded containers and thereafter reduce or destroy the bacteria on that portion of the foodstuffs with which it comes into contact. Plastic sheeting for food wrappers and plastic containers are only two specific applications for the composition of the present invention.

The prior art discloses a number of examples of plastic materials containing antimicrobial agents, but none have the particular characteristics of the present invention.

For instance, U.S. Pat. No. 5,554,373 to Seabrook et al., which is incorporated herein by reference in its entirety, discloses compositions containing antimicrobial agents and a chemical controller, which functions to regulate the release rate of the antimicrobial agent. One of the biocidal agents disclosed is 10,10-oxybisphenoxarsine, which is an organically bound arsenic and will be referred to hereinafter as OBPA.

U.S. Pat. No. 4,888,175 to Burton, et al., discloses a plastic packaging material having a biocidal agent dissolved or dispersed therein. The biocidal agent disclosed is OBPA. The plastic material can be formed into a package for containing an organic material susceptible to bacterial or viral attack.

U.S. Pat. No. 4,666,956 to Spielau, et al. discloses a biocidal composition based on organic arsenic compounds. A tin compound is added to the composition to prevent elution of the arsenic compound. The compositions are used in the production of molded plastic articles, especially those vulnerable to biological attack.

U.S. Pat. Nos. 4,624,679 and 4,891,391, both to McEntee, disclose an antimicrobial and anti-oxidant composition preferably incorporated into a thermoplastic resin. The antimicrobial agents are incorporated into the thermoplastic materials during fabrication so that the resulting thermoplastic articles will resist microbial growth. The anti-oxidant is added so that the antimicrobial agent does not degrade during processing. OBPA is disclosed as one of the microbiocides.

An assortment of compositions containing microbiocides are disclosed in U.S. Pat. Nos. 4,686,239, 4,789,692, 4,086, 297, and 4,663,077 in which Rei is listed as an inventor. In the '239 patent, the '692 patent, and the '297 patent, a composition is disclosed wherein a microbiocide in high concentrations is added to a thermoplastic resin. The resulting concentrate is then incorporated into a second thermoplastic resin to produce a resulting article having the appropriate level of microbiocide. The second thermoplastic resin is added in an attempt to control the mobility of the microbiocide. One of the microbiocides disclosed is OBPA.

The '077 patent discloses a microbiocidal solution comprising an aryl alkanol solvent and a microbiocide compound dissolved therein. A plasticizer suitable for use as a polymer processing aid is added to the composition.

Anti-bacterial materials and antimicrobial mixtures are disclosed in United Kingdom Patent No. 1,169,288 and European Patent Application No. 84113170.9. The United Kingdom patent is directed to a material having a base sheet of plastic coated on one surface with a polymeric liquid composition containing an anti-bacterial agent capable of migrating through the sheet. The European patent application, on the other hand, discloses a mixture of a phenoxyarsine as an antimicrobial agent and a solvent. A plasticizer can be added to the mixture for incorporation into plastics.

Other prior art compositions containing biocides include U.S. Pat. No. 4,747,902 to Saitoh, U.S. Pat. No. 3,864,468 to Hyman et al., U.S. Pat. No. 4,666,706 to Farquharson et al., U.S. Pat. No. 5,063,706 to Aki et al., and U.S. Pat. No. 4,876,070 to Tsukahara et al.

Although the prior art shows a combination of biocidal compositions, the particular features of the present invention remain absent. Some of the prior art discloses materials containing small amounts of biocidal compositions for preventing bacterial attack on the material itself. However, most of the prior art does not show the use of biocidal materials in packaging films or sheets at a level such that the contents of the package, instead of the plastic itself, are inhibited against bacterial or viral growth. Further, the prior art is generally deficient in affording a composition that will not only control bacterial growth, but will also simultaneously control the growth of fungi, viruses, and parasites.

Although it is known in the prior art to incorporate antimicrobial agents into plastics, the plastic products generally cannot be used for food applications unless extremely small amounts of biocides are used because the biocides may be harmful to humans. However, small quantities of biocide will not protect the contents of the package adequately or protect the contents for an effective length of time from attack. Consequently, a need exists for a polymeric material containing antimicrobial agents which is safe for human and animal contact and which is safe for contact with human and animal consumables. Further still, although some of the prior art discloses the incorporation of antimicrobial agents with activity specifically against bacteria, a need exists for an antimicrobial composition that will simultaneously inhibit the growth of fungi, viruses, actinomycetes and parasites, as well as bacteria.

SUMMARY OF THE INVENTION

The present invention recognizes and addresses the foregoing disadvantages, and others of prior art constructions and methods.

Accordingly, one object of the present invention is to provide an antimicrobial composition.

Another object of the present invention is to provide an antimicrobial composition containing phytochemicals or phytonutrients which may include essential oils.

Another object of the present invention is to provide a polymeric composition containing antimicrobial agents.

Another object of the present invention is to provide a polymeric composition containing antimicrobial agents that will destroy bacteria, viruses, parasites, and fungi.

Another object of the present invention is to provide a method for the release of the biocidal ingredient from the antimicrobial agent in a polymeric composition.

The present invention achieves the foregoing and other objectives by providing an antimicrobial agent which when added to polymeric materials destroys or inhibits the growth of microorganisms. The antimicrobial agent includes a biocide. Of particular advantage, the biocide included in the invention may be a naturally occurring phytonutrient or phytochemical or it may be a chemical compound shown to be safe for contact with human consumables. As used herein, a phytochemical refers to a naturally occuring chemical or compound derived or extracted from an organism, such as a plant.

In one embodiment, the antimicrobial agent of the present invention may be added to a polymeric substrate in combination with a migration control agent which controls the rate at which the antimicrobial agent is released from the plastic or, alternatively, with a chemical releaser which facilitates release of the antimicrobial agent. For instance, Vitamin E may be added to the polymer substrate in order to control the migration and release of the antimicrobial agent, such as is claimed in the present inventor's previous patent (U.S. Pat. No. 5,554,373) as referenced above. Included in the present invention, is the fact that Vitamin E, itself, possesses antimicrobial properties.

Alternatively or in addition to using Vitamin E, citric acid may also be added to the polymer substrate. Citric acid, which is also an effective antimicrobial agent, has been found to facilitate the release of some antimicrobial agents.

For many applications, the antimicrobial agents of the present invention are incorporated into a polymeric composition such that the active concentration of the antimicrobial agent is at a level capable of inhibiting the growth of microorganisms but is also at a level safe for human handling and consumption and for contact with consumables.

As used hereinafter, the term active concentration refers to the concentration of the antimicrobial agents that are available for destroying and inhibiting the growth of microorganisms. The active concentration further refers to the antimicrobial agents that have been released from the materials in which they are contained. Also, the term consumables as used hereinafter is defined as any food product, including, but not limited to, agricultural products. Consumables also refers to all drinkable liquids including water.

The present invention is directed to a biocide for adding to polymeric materials for protecting such materials and other items in close proximity thereto from attack and infestation of microorganisms. In one embodiment, the biocide of the present invention may include capsaicinoids, which are phytochemicals derived from the fruit of Capsicum frutescens. Capsaicinoids can inhibit or destroy bacteria, viruses, and fungi. Available commercially as oleoresin capsicum, capsicum can be added to a polymer in a liquid carrier or can be incorporated via dry soluble carriers such as salt or dextrose. Preferably, a 4% (weight/volume) solution of capsicum is added to an equal volume of a vegetable oil, such as soybean oil and particularly epoxidized soybean oil, with the resulting mixture being added to the polymer during extrusion. The capsicum can be added as a 4% solution to polymeric materials in an amount from about 0.05 ppm to about 10 ppm, for food applications; from about 10 ppm to about 100,000 ppm, for industrial applications; and as solutions of 2%, 4%, 12% or 14%, from 0.05 ppm to about 50,000 ppm, for medical and agricultural applications.

In an alternative embodiment, the biocide may include grapefruit seed extract, which exhibits anti-bacterial, anti-parasitic, and anti-fungal activity. The grapefruit seed extract, available commercially as CITRICIDAL, can be added in a liquid carrier. The liquid carrier can be propylene glycol, polyethylene glycol, or silicone. For example, the grapefruit seed extract can be mixed with propylene glycol, preferably in a 1:1 ratio, before being added to polymeric materials. The grapefruit seed extract can be added to polymeric materials alone, in combination with other biocides, in combination with citric acid, and in combination with Vitamin E. The grapefruit seed extract can be added to polymeric materials in an amount from about 5,000 ppm to about 30,000 ppm for food applications; from about 20,000 ppm to about 50,000 ppm for industrial applications; from 5,000 ppm to about 30,000 ppm for medical applications, and from about 5,000 ppm to about 50,000 ppm for agricultural applications.

In yet another alternative embodiment, the biocide may be a phytochemical-derived formula, commercially known as BIOCIDIN, which exhibits antifungal, anti-bacterial and anti-parasitic activity. The BIOCIDIN formula contains: chlorophyll, impatiens, pallida, hydrastis canadensis, ferula galbanum, hypericum perforatum, villa rubris, fumaria, frasera carolinesis, gentiana campestris, sanguinaria, allicin and garlic. BIOCIDIN can be added alone or in combination with other biocides, with Vitamin E, or with chemical releasers, such as citric acid. Further, BIOCIDIN may be added to a polymer carrier, such as an Epoxidized Soybean Oil (ESO) or an Epoxidized Vegetable Oil (EVO). BIOCIDIN may be added to polymeric materials in an amount from about 2,000 ppm to about 25,000 ppm for food applications; from about 2,000 ppm to about 25,000 ppm for medical applications; from about 5,000 ppm to about 50,000 ppm for industrial applications; and from about 5,000 ppm to about 50,000 ppm for agricultural applications.

In yet another embodiment, the biocide may be Lemon Grass Oil which is another phytochemical. Lemon Grass Oil is a natural by-product of lemon grass and is extracted by steam and other nontoxic extraction methods. Lemon Grass Oil exhibits anti-fungal and anti-bacterial activity. The Lemon Grass Oil may be added to polymeric substrates alone or in combination with other biocides, migration controllers such as Vitamin E, or releasers, such as citric acid, or may be added to a polymer carrier such as ESO or EVO. The Lemon Grass Oil may be added to the polymeric materials in an amount from about 2,000 ppm to 20,000 ppm for food applications; from about 5,000 ppm to about 50,000 ppm for industrial applications; from about 2,000 ppm to about 50,000 ppm for medical applications and from about 2,000 ppm to about 50,000 ppm for agricultural applications.

In another alternative embodiment, the biocide may be Tea Tree Oil, which is also a phytochemical. Tea Tree Oil is a natural by-product of the tea tree, (melaleuca species). Tea Tree Oil is extracted through natural non-toxic precesses such as steam. Tea Tree Oil exhibits anti-fungal and anti-bacterial activity. Tea Tree Oil may be added to polymeric substrates alone or in combination with other biocides, migration controllers such as Vitamin E or releasers such as citric acid, and may be added to a polymer carrier, such as ESO or EVO. Tea Tree Oil may be added to the polymeric materials in an amount from about 2,000 ppm to about 20,000 ppm for food applications; from about 5,000 ppm to about 50,000 ppm for industrial applications; from about 2,000 ppm to about 50,000 ppm for medical applications and from about 2,000 ppm to about 50,000 ppm for agricultural applications.

In yet another alternative embodiment, the biocide may be a chemical biocide, which has been shown to be safe when used in contact with food. For instance, the chemical biocide may be trichloromelamine (N-chloro-p-toluenesulfonamide sodium salt-trihydrate), which exhibits bacteriocidal activity against both gram positive and gram negative bacteria. Trichloromelamine can be added as a powder or in a liquid carrier, such as epoxidized soybean oil, vegetable oil or propylene glycol. Trichloromelamine can be added as a 60% (weight/volume) concentration to polymeric materials. The trichloromelamine may be added alone or in combination with other agents, including phytochemical biocides and with or without citric acid to facilitate the release of the active biocidal agent in trichloromelamine or to control a broader range of microbes. Trichloromelamine can be added to polymeric materials in an amount from about 50 ppm to about 50,000 ppm, preferably in an amount from about 50 ppm to about 5000 ppm for food applications; and from about 10,000 ppm to about 50,000 ppm for industrial, medical, or agricultural applications.

In another alternative embodiment, the biocide may be zinc pyrithione, which exhibits anti-bacterial activity. The zinc pyrithione may be added to polymeric materials alone or in combination with other biocides, and with or without Vitamin E. The zinc pyrithione can be added to polymeric materials in an amount from about 5,000 ppm to about 30,000 ppm for food applications; from about 20,000 ppm to about 50,000 ppm for industrial applications; from about 5,000 ppm to about 30,000 ppm for medical applications; and from about 5,000 ppm to about 50,000 ppm for agricultural applications.

Another group of chemical biocides that may be used according to the present invention and which have been shown to be relatively safe are the quaternary ammonium compounds. For instance, particular examples of quaternary ammonium compounds that may be incorporated into polymers for providing the polymers with antimicrobial properties are alkyl dimethyl benzyl ammonium chloride (ADBAC), dialkyl dimethyl ammonium and alkyl dimethyl ethybenzyl ammonium chlorides.

As described above, the present invention includes a chemical releaser, which is used to facilitate the release of the antimicrobial agents from the polymeric material. In particular, in some applications, the chemical releaser allows the active ingredient contained in the antimicrobial agent to be released from the polymeric substrate. The releaser may be citric acid, a phytochemical which also exhibits anti-bacterial activity. For example, citric acid can facilitate the release of chlorine from tricloromelamine embedded in polymeric materials, resulting in an increase in the active concentration of the biocidal agent. Citric acid extract can be added in a liquid carrier. The liquid carrier can be propylene glycol. Citric acid extract can be added to polymeric materials alone or in combination with other biocides. Citric acid extract can be added to polymeric materials in an amount from about 5,000 ppm to about 30,000 ppm for food applications; from about 20,000 ppm to about 50,000 ppm for industrial applications; from 5,000 ppm to about 20,000 ppm for medical applications, and from about 5,000 ppm to about 50,000 ppm for agricultural applications.

It should be understood that the present invention is generally directed to the use of biocides in polymeric substrates such as phytochemical biocides and other antimicrobial agents that have been proven to be safe when used in contact with food items. The various biocides and antimicrobial agents mentioned above, represent various preferred embodiments of the present invention. The amounts and concentrations listed above are also merely exemplarily and may be increased or decreased depending upon the particular application. Other biocides that may be used in the process of the present invention will be discussed in greater detail below.

The polymeric material that can be combined with the biocides of the present invention include, for instance, silicone products, such as N-propylsilicate, a polyalkylene, a polyolefin, a polyvinyl, a synthetic rubber, a latex fiber, a synthetic fiber, or mixtures thereof.

Once a biocide has been incorporated into a polymeric material in accordance with the present invention, the polymeric material can be formed into various articles for a limitless variety of applications. For instance, the article can include plastic sheeting wherein the antimicrobial agents can prevent the growth of microorganisms on the sheeting or in contact with the sheeting. The article can also be in the form of agricultural granules for protecting agricultural products from attack by microorganisms or can take the shape of a plant container for protecting a plant from microbial attack.

The present invention is further directed to a method of controlling the release of antimicrobial agents from a polymeric composition. The method includes the steps of providing a polymeric material capable of being formed selectively into granules, films, sheets, tubing and other various articles. Antimicrobial agents, such as capsicum, grapefruit seed extract, citric acid, BIOCIDIN, Lemon Grass Oil, Tea Tree Oil, Vitamin E, zinc pyrithione, quaternary ammonium compounds and trichloromelamine, can be incorporated into the polymeric material. In particular, the antimicrobial agents are incorporated into the polymeric material in an amount so as to prevent or inhibit the growth of microorganisms on or in close proximity to the polymeric material.

Other objects, features, and aspects of the present invention are discussed in greater detail below.

BRIEF DESCRIPTION OF THE DRAWINGS

A full and enabling disclosure of the present invention including the best mode thereof to one of ordinary skill in the art, is set forth more particularly in the remainder of the specification, including reference to the accompanying figures in which.

Figure 1:
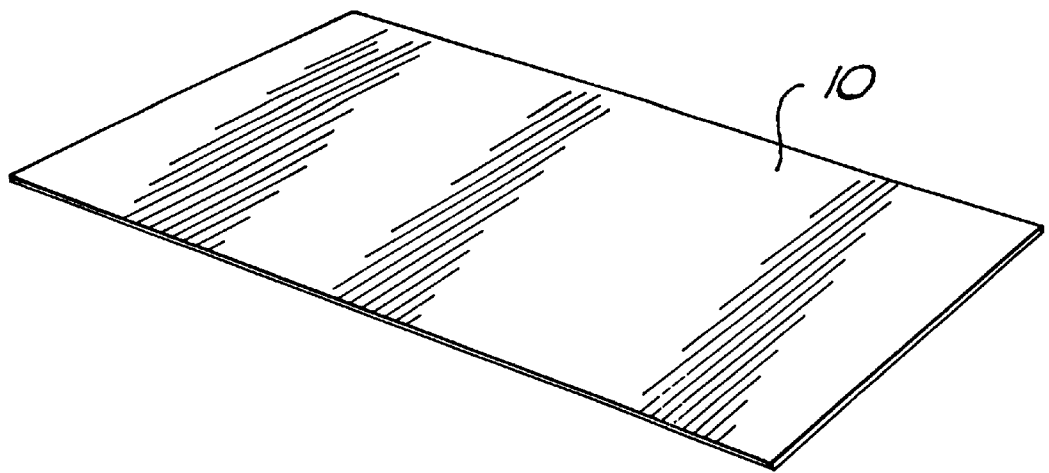
FIG. 1 is a plan view of a sheet prepared in accordance with the present invention.

Repeat use of reference characters in the present specification and drawings is intended to represent same or analogous features or elements of the invention.

DETAILED DESCRIPTION OF PREFERRED EMBODIMENTS

In general terms, the present invention is directed to polymeric compositions containing antimicrobial biocides and methods of making and using the same. The rate of migration or the release of the biocidal ingredient from the antimicrobial agent embedded in the polymeric composition may be affected by using a chemical releaser such as citric acid, or a migration controller such as Vitamin E. One of the important advantages of the present invention is that the composition can be made into plastic articles to protect food products, house plants, or act as water lines. In one embodiment, the antimicrobial agents are extracted from naturally occurring substances, such as phytochemicals. These agents may be safer to use in direct contact with foodstuffs than conventional antimicrobial drugs. Besides phytochemicals, however, the present invention is also directed to the use of various other antimicrobial agents.

The composition of the present invention is directed to a base polymeric material containing a single or a mixture of biocidal agents. Preferably, these antimicrobial agents are dispersed within the polymeric base composition. Particular examples of antimicrobial agents include phytochemicals such as capsaicinoids, grapefruit seed extract, BIOCIDIN, Lemon Grass Oil, Tea Tree Oil, citric acid, Vitamin E and various other antimicrobial agents that are believed to be safe for human handling and contact, such as trichloromelamine, quaternary ammonium compounds and/ or zinc pyrithione.

Citric acid extract is obtained from a variety of sources, any particular form of which can be used in the present invention. Citric acid extract may facilitate the release of the biocidal ingredient from an antimicrobial composition. One particular class of compounds whose release is facilitated by citric acid extract according to the present invention is trichloromelamine (N-chloro-p-toluenesulfonamide sodium salt-trihydrate). Trichloromelamine is the active ingredient in a variety of disinfectant formulations, and is approved by the Environmental Protection Agency (EPA) for use on food-contact surfaces. One commercial source for trichloromelamine is from H & S Chemical Company (Cincinnati, Ohio; EPA Reg. No. 65169-1).

Trichloromelamine does not migrate well from polymers when extruded into the polymer. However, the addition of citric acid to the polymeric composition causes the release of trichloromelamine from the polymer matrix.

Another type of biocidal agent according to the present invention is grapefruit seed extract, an effective antimicrobial agent for inhibiting the growth of a plurality of microorganisms. Particularly, grapefruit seed extract is an effective phytochemical biocide against bacteria, fungi, and some parasites. Grapefruit seed extract is available commercially as CITRICIDAL, from Bio/Chem Research (Lakeport, Calif.).

Another class of compounds found to be effective phtochemical biocidal agents are the major capsaicinoids.

Capsaicinoids are known to inhibit or destroy bacteria, viruses, and fungi. One particular source of capsaicinoids is oleoresin capsicum, available commercially from Kalsec (Kalamazoo, Mich.).

In a preferred composition of the present invention, oleoresin capsicum is extruded into the polymeric material. The resulting composition will destroy or inhibit the growth of bacteria, viruses, and fungi. This is particularly important because, in many applications, the object that is to be protected from microbial infestation is subject to attack from more than one variety and species of microorganisms.

In alternative embodiments of the present invention, other antimicrobial agents such as BIOCIDIN, Lemon Grass Oil, Tea Tree Oil, zinc pyrithione and quaternary ammonium compounds such as alkyl dimethyl benzyl ammonium chloride, dialkyl dimethyl ammonium, and alkyl dimethyl ethybenzyl ammonium chlorides may be added to polymeric materials as biocidal agents. The following table is illustrative of some of the microorganisms that may be inhibited by the present invention.

Fungi
*Aspergillus flavus*
*A. fumigalus*
*A. niger*
*Blastomyces dermatitidis*
Candida spp.
*Coccidioides immitis*
*Cryptococcus neoformans*
*Fusarium culmorum*
Geotrichum spp.
*Histoplasma capsulatum*
*Malassezia furfur*
Microsporum spp.
*Mucor racemosus*
Nocardia spp.
*Paracoccidioides brasiliensis*
Penicillium spp.
*Rhizopus higricans*
*Saccharomyces cerevisiae*
*Sporothrix schneckii*
Torulopsis spp.
Trichophyton spp.
Bacteria
*Aerobacter aerongenes*
*Aeromonas hydrophila*
*Bacillus cereus*
*Bacillus subtilis*
*Bordetella pertussis*
*Borrelia burgdorferi*
*Campylobacter fetus*
*C. jejuni*
*Corynebacterium diphtheriae*
*C. bovis*
*Desulfovibrio desulfurica*
*Escherichia coli* 0157:H7
Enteropathogenic *E. coli*
Enterotoxin-producing *E. coli*
*Helicobacter pylori*
*Klebsiella pneumoniae*
*Legionella pneumophila*
*Leptospira interrogans*
*Mycobacterium tuberculosis*
*M. bovis*
*Neisseria gonorrhoeae*
*N. meningitidis*
*Proteus mirabilis*
*P. vulgaris*
*Pseudomonas aeruginosa*
*Rhodococcus equi*
*Salmonella choleraesuis*
*S. enteridis*
*S. typhimurlum*
*S. typhosa*
*Shigella sonnei*
*S. dysenteriae*
*Staphylococcus aureus*
*S. epidermidis*
*Streptococcus anginosus*
*S. mutans*
*Vibrio cholerae*
*Yersinia pestis*
*Y. pseudotuberculosis*
Actinomycetes
*Stretomyces reubrireticuli*
*Streptoverticillium reticulum*
*Thermoactinomyces vulgaris*
Viruses
Adenoviruses
Coronaviruses
Cytomegalovirus
Enteroviruses
Epstein-Barr virus
Herpes simplex virus
Hepatitis viruses
Human Immunodeficiency virus
Human Parvoviruses
Influenza viruses
Morbillivirus
Mumps virus
Norwalk viruses
Papillomaviruses
Paromyxovirus
Poxvirus
Rabies virus
Reoviruses
Rotaviruses
Rubella virus
Respiratory Synctial virus
Rhinoviruses
Varicella zoster virus
Parasites
*Ancyclostoma braziliense*
Anisakis
*Babesia microti*
*Balantidum coli*

*Blastocystis hominis*
*Chilomastix mesnili*
*Cryptosporidium parvum*
Cyclospora
*Dientamoeba fragilis*
*Diphyllobothrium latum*
*Echinococcus granulosus*
*Entamoeba coli*
*E. histolytica*
Enterocytozoon
*Fasciola hepatica*
*Giardia lamblia*
*Iodamoeba butschlii*
*Isospora belli*
*Leishmania brasiliensis*
*L. donovani*
*L. tropica*
*Paragonimus westermani*
*Plasmodium vivax*
*Pnemocystis carinii*
*Sarcocytis hominis*
*Strongyloides stercoralis*
*Taenia solium*
*Toxoplasma gondii*
*Trichomonas vaginalis*
*Trichinella spiralis*
*Trypanosoma cruzi*

The compositions of the present invention can be used in an almost limitless variety of applications. Generally, the compositions are well suited for applications where it is desirous to prevent the growth of microorganisms upon the polymeric material itself or on products in close proximity to the material. For instance, the composition can be incorporated into a container or a film for protecting the contents thereof. The following is a list of possible applications. The list is not exhaustive but is merely provided for illustrative purposes.

Floral Uses
Plastic floral buckets
Bucket liners
Corsage bags
Shredded plastic for box packing and shipping
Starter trays
Florafoam blocks
Shipping and display bags for bulbs
Industrial Uses
Containers and liners for industrial manufacturing
Shredded plastic for packaging perishables
Industrial pipe lining such as oil, gas and water lines
Nuclear and hydroelectric cooling towers
Water and sewer treatment facilities
Aircraft fuselage interiors
NASA applications for space
Cat liter boxes and liners
Marine Uses
Ship and boat hulls
Ship and boat decks and other fouling surfaces
Buoys and mariner floating docks
Specific Naval applications, such as optically clear underwater surfaces
Marine rope and cable
Agricultural Uses
Row crop plastic mulch
Drip irrigation and related components
Shredded Easter grass for packaging
Seedling starter trays
Seedling starter growing blocks
Greenhouse related plastic components
Granular mix for growing mediums
Drip irrigation tubing
Various plastic containers
Plastic row crop tunnels
Food packaging, wrap containers
Retail display containers, trays, racks
Vacuum and shrink wrap
Medical and Dental Uses
Catheters
Shunts
Eye buckles
Contact lenses
Bandages
Dust covers, surgical drapes
Bed liners
Isolation gowns, caps and shoe covers
Clean room apparati
Counter tops, walls and floors
Orthopaedic appliance packaging
Implants
Miscellaneous Products
Animal litter additive (granular)
Animal litter container liners
Veterinary products
Hygiene disposal bags Many different types of polymeric materials may be used in the present invention. A polymeric material is preferably chosen that can be formed into films, sheets, containers, tubes, granules, coatings, and laminates besides having the ability to be formed into other articles. The antimicrobial agents as discussed herein have been found to be compatible with a wide variety of polymers, plastics, and other materials. Preferably, the antimicrobial agents are placed into a hydrocarbon based material, such as by extrusion. Examples of such polymeric materials include polyalkylenes, polyolefins, polyvinyls, synthetic rubber, latex fiber, synthetic fiber, and mixtures thereof. Other useful polymers include polyethylenes, polypropylenes, polystyrenes, polyacrylates, polyvinylchlorides, polyurethanes, and mixtures thereof. The base material can further include homopolymers or copolymers. The particular polymer used depends mostly upon the application. For instance, polyethylene or polyvinylchloride are preferably used in plastic sheeting because of its flexibility and physical characteristics.

The amounts of the biocidal agents added to the composition are also dependent upon the particular application. Factors to consider are the conditions under which the composition is to be used, the microorganisms to be inhibited, the duration of the use, whether the object to be protected is a consumable, and the active concentration of the antimicrobial agents that is desired. For example, capsicum can be added in an amount from about 1 ppm to about 100,000 ppm, depending upon the desired application. For a food application, capsicum could be added to the polymeric material in an amount from about 0.05 ppm to about 10 ppm.

It should be understood that the present invention is broadly drafted, in one embodiment, towards incorporating phytochemicals as biocidal agents into polymeric materials. In several preferred embodiments of the present invention, capsicum, citric acid extract, and grapefruit seed extract may be used as biocidal agents. The present invention, however, encompasses the use of many other biocidal agents. The following, although illustrative of other examples of phytochemicals that can be incorporated as biocides, is not meant to be an all-inclusive list: *Jasonia candicans* (sesquiterpenes, lactones); *Polygonum flaccidum* (flavone and alpha santalene derivatives); *Acalypha wikesiana* (extracts); *Pavetta owariensis* (procyanidins); *Plectranthus hereroensis* (diterpenoids, diterpenes); Moss (Dicranin extract); *Cannabis sativa* (extract); Gloiosiphonia spp. (gloiosiphones); Laminaceae spp. (extract); Securidaca spp. (extract); Veronia spp. (extract); *Hyptis umbrose* (umbrosone); *Asclepias syriaca* (milkweed extract); *Tagetes tenuifolia* (thiophene); *Calophyllum inophylloide* (flavonoids); *Tanacetum densum* (sesquiterpene lactones, triterpenoids); *Neorautanenia mitis* (extract); *Premna schimper* (diterpene); *Premna oligotricha* (sesquiterpenes); *Premna oligotricha* (diterpenes); *Jasonia candicans* (essential oils); *Visnea mocanera* (beta-sitosterol, triterpenic betulinic acid, ursolic acid, plantanic acid); Asteraceae spp. (terthiophenes and polyynes); *Petalostemum purpureum* (extract); *Camelia sinensis* (catechin); *Helichrysum picardii* (flavonoids); *Helichrysum italicum* (flavonoids); *Corydalis pallida* (protoberberine alkloids); *Shiraia bambusicola* (perylenequinones); *Fraxinum ornus* (hydroxycoumarins); *Podocarpus nagi* (totarol and nortiterpene dilactones); *Heterotheca inuloides* (sesquiterpenoids); Pelargonium spp. (essential oils); *Piper sarmentosum* (phenylpropanoids); Allium spp. (extract); *Juniperus procera* (diterpenes); *Achillea conferta* (flavonoids, flavones, sesquiterpenoid lactones); *Magnolia virginiana* (lignans, neolignans); *Eucalyptus euglobal* (euglobal); *Armillaria mellea* (armillaric acid); *Dracena mannii* (spirostanol saponin); *Piper aduncum* (chromenes, prenylated benzoic acid); Rhamnaceae spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); Paepalanthus spp. (vioxanthin); *Helichrysum stoechas* and *Helichrysum crispum* (extracts); *Achillea ptarmica* (trans-pinocarveyl hydroperoxides); *Dehaasia incrassata* (alkaloids); Asteraceae spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative), *Celosia argentea* (triterpenoid saponins and flavonoids); *Azadirachta indica* (tetranortriterpenoid, mahmoodin, protolimonoids, naheedin); Moraceae spp. (coumarins); *Hypericum erectum* (phloroglucinol derivatives); *Podospora appendiculate* (Appenolides A, B, & C, furanones); *Artemisia princeps* var. *orientalis, Artemisia capillaris, Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borrieria latifolia, Borreria setidens, Hedyotis diffusa*), *Hedyotis nudicaulis, Morinda elliptica, Morinda umbellata, Sida rhombifolia,* and *Vitex ovata* (extracts); *Tabebuia impetiginosa*, Achyrocline spp., *Larrea divaricata, Rosa borboniana, Punica granatum, Psidium guineense, Lithrea ternifolia* (extracts); *Lepechinia caulescens, Lepidium virginicum* and *Tanacetum parthenium* (extracts); *Talaromyces flavus* (extracts); *Daucus carota* (extract); *Flabellia petiolata, Caulerpa prolifera, Halimeda tuna, Corallina elongata, Lithophyllum lichenoides, Phyllophora crispa*, Cystoseira spp., Halopteris spp., Codium spp., *Valonia utricularis, Posidonia oceanica, Zostera noltil* and *Cymodocea nodosa* (extracts); *Centauraea orientalis, Diospyros khaki, Sida hermaphrodita, Forsythia intermedia, Scutellaria polydon, Eugenia malaccensis* and *Eugenia jambolana* (extracts); Fritillaria L. spp. (ebeinone, steroidal alkaloids); *Kigelia pinnata, Peperomia pellucida, Populus nigra, Populus balsamifera* and *Populus deltoides* (extracts); *Melaleuca alternifolia* (essential oil); *Elfvingia applanata* (naringenin); *Ficus sycomorus*, grapefruit seed, Garlic, Allicin, Peat, *Strophanthus hispidus, Secamone afzeli, Mitracarpus scaberi, Entada abyssinjca, Terminalia spinosa, Harrisonia abyssinica, Ximinea caffra, Azadirachta indica, Spilanthes mauritiana, Terminalia spinosa* (extracts); Cyanobacteria (ambigols A and B, tjipanazole); coffee (extract); *Sporochnus pedunculatus, Dalbergia melanozylon, Celastrus scandens, Juglans nigra, Kalmia latifolia, Pelargonium xhortorum, Rhus glabra* and *Lindera benzoin* (extracts); *Striga densiflora, Striga orobanchioides, Striga lutea, Pistacia lentiscus L., Mitracarpus villosus, Bixa orellana, Bridelia ferruginea, Alpinia katsumadai, Alpinia officinarum, Artemisia capillaris, Casia obtusifolia, Dendrobium moniliforme, Epimedium grandiflorum, Glycyrrhiza glabra, Lithosperum erythrorhizon, Magnolia obovata, Morus bonbycis, Natopterygii incisium, Polygonum multiflorum, Prunus mume, Rheum palmatum, Ricinus communis, Sophora flavescens, Swertia japonica*, black pepper, rosemary, red pepper, *Isopyrum thalictroides, Calotropis procera*, Chrysanthemum spp., *Holarrhena antidysenterica, Lunularia crusiata, Dumertiera hirsuta, Exormotheca tuberifera,* and liverwort (extracts); *Filipendula ulmaria, Salix glauca, Usnea filipendula, Clkadina arbuscula* (salicylic compounds); *Tanacetum parthenium, Thymus capitatus,* and *Elfingia applanata* (extracts); *Fraxinus ornus* (hydroxycoumarins, esculin, esculetin, fraxin, and fraxetin); *Zizyphus nummularia*, LONGO VITAL, Pelargonium spp., *Scaevola sericea, Psychotria hawaiiensis, Pipturus albidis, Aleurites moluccana, Solanum niger, Piper methysticum, Barringtonia asiatica, Adansonia digitata, Harungana madagascariensis, Jacaranda mimosaefolia, Erythroxylum catauba, Bidens pilosa, Lemna minor*, Potamogeton spp., *Nasturtium officinale, Apium nodiflorum, Agaricus subrutilescens, Amanita virosa, Amanita pantherina, Lycoperdon perlatum, Psidium guajava, Averrhoa carambola, musa sapientum, Carica papaya, Passiflora edulis, Lansium domesticum* and *Baccaurea motleyana* (extracts); horse radish, celandine grass, bur marigold and yarrow grass (extracts); *Abuta grandifola, Cyperus articulatus, Gnaphalium spicatum, Pothomorphe peltata, Ficus sycomorus, Ficus Benjamina, Ficus bengalensis, Ficus religiosa, Alchornea cordifolia, Bridelia feruginea, Eucalyptus citriodora, Hymenocardia acida, Maprounea africana, Monachora arbuscula, Tedania ignis*, Arenosclera spp., *Amphimedon viridis, Polymastia janeirensis, Aplysina fulva, Pseudaxinella lunaecharta, Nelumbium speciosum* and *Mycale arenosa* (extracts); cloves (eugenol acetate and iso-eugenol); *Chrysthanemum boreale* (sesquiterpenoid lactones); *Eucalyptus globolus,*

*Punica granatum, Bocconia arborea, Syzygium brazzavillense, Syzygium guineense, Carthamus tinctorius*), *Ginkgo biloba, Mosla chinensis, Salvia officinalis,* and *Cinnamomum cassia* (extracts); *Cryptolepis sanguinolenta* (alkaloids, cryptolepine); *Chelidonium majus* (alkaloids, berberine, coptisine); Vitex agnus-castus (extract); *Cladonia substellata* (usnic acid); *Fuligo septica, Tubifera microsperma* (extract); *Mundulea monantha, Tephrosia linearis* (flavonoids); *Lpomoea fistulosa* (extract); *Pimenta dioica* (essential oils); *Ratibida latipalearis, Teloxys graveolens, Dodonaea viscosa, Hypericum calycinum, Hyptis albida, Hyptis pectinata, Hyptis suaveolens* and *Hyptis verticillata* (extracts); *Asteriscus graveolones* (bisabolone hydroperoxides); *Derris scandens, Alnus rubra,* Araliaceae family (extracts); *Vinca rosea,* Australian tea tree oil, peppermint oil, sage oil, thymol, eugenol and *Thuja orientalis* (extracts); *Anacardium occidentale* (phenolic lipids); *Oidiodendron tenuissimum* (extract); *Acacia nilotica* and *Acacia farnesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla, Chamaesyce hirta, Baccharis glutinosa* and *Larrea tridentata* (extracts); *Camelia sinensis* and *Euphorbia hirta* (theaflavin, polyphenon 60); *Tabernaemontana pandacaqui, Yucca shidigera, Hemistepa lyrata, Yougia japonica, Prunella vulgaris, Lamium amplexicaule, Juniperus chinensis, lxeris dentata, Gnaphalium affine, Chelidonium majus, Spirea prunifolia, Erythronium japonicum, Taxus wallichiana, Ganoderma lucidum Drava nemorosa, Youngia capillaris, Equisetum arvense,* Australiam Lavender, Black Seed, *Catuaba casca,* Cineole, Damiana, *Dicranum scoparium,* Eucalyptus oil, Ginger, and Grape seed (extracts); Neem seed, bark, and leaf extract; Neem oil; New Zealand Manuka extract; *Nicotiana tabacum* extract; olive leaf extract; a-pinene and b-pinene extracts; Rhubarb root extract; *Syringa vulgaris* extract; Tea tree oil (Terpinen-4-ol, a-terpinene, y-terpinene, a-terpineol, Terpinolene); Thyme (extract) and Vitamin E (extract).

When making the compositions of the present invention, the hydrocarbon base material may or may not be heated. The biocidal agents, chemical releasers, and migration controllers are then added either together or one at a time (if more than one agent is employed in the biocide). The mixture is then mixed until the biocidal agents and the chemical releasers are evenly dispersed within the polymeric composition. Other additives, such as plasticizers and dyes, can be added without affecting the biocidal agents or the chemical releasers. In fact, some plasticizers or other ingredients may be added to enhance the resulting physical characteristics of the composition. Accelerators such as ethylene methyl acrylate (EMA) may also be added.

The resulting composition can be extruded, blown, or molded into various articles as listed above. The following is a list of products that may incorporate the composition of the present invention.

One particular product incorporating the composition of the present invention as illustrated in FIG. 1 is plastic sheeting shown generally as 10. Sheet 10 can then be formed into various packages and articles. For instance, sheet 10 can be used to make cat litter boxes. In one embodiment, a cat litter box contains capsicum in an amount of approximately 5 ppm, grapefruit seed extract in an amount of approximately 25,000 ppm and BIOCIDIN in an amount of approximately 10,000 ppm.

Figure 2:
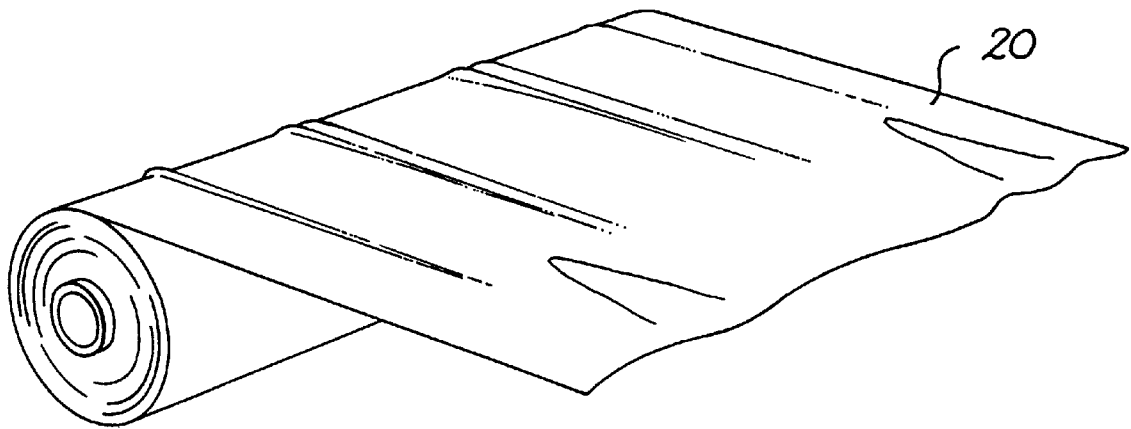
FIG. 2 is a perspective view of a roll of polymeric film made in accordance with the present invention.

Referring to FIG. 2, the composition of the present invention can also be incorporated into a film 20. Film 20 can be used for a variety of liners and wraps. One of the biggest problems faced by shippers and exporters of fresh produce is the relatively short life of fresh fruits and vegetables. Many produce items are shipped great distances, requiring a significant amount of travel time. Film 20 can be used to wrap fruits and vegetables for increasing their shelf life by protection from microbial infestation. Film 20 can also be used to wrap meat to increase its storage life and to inhibit microbial organisms present after processing.

Figure 3:
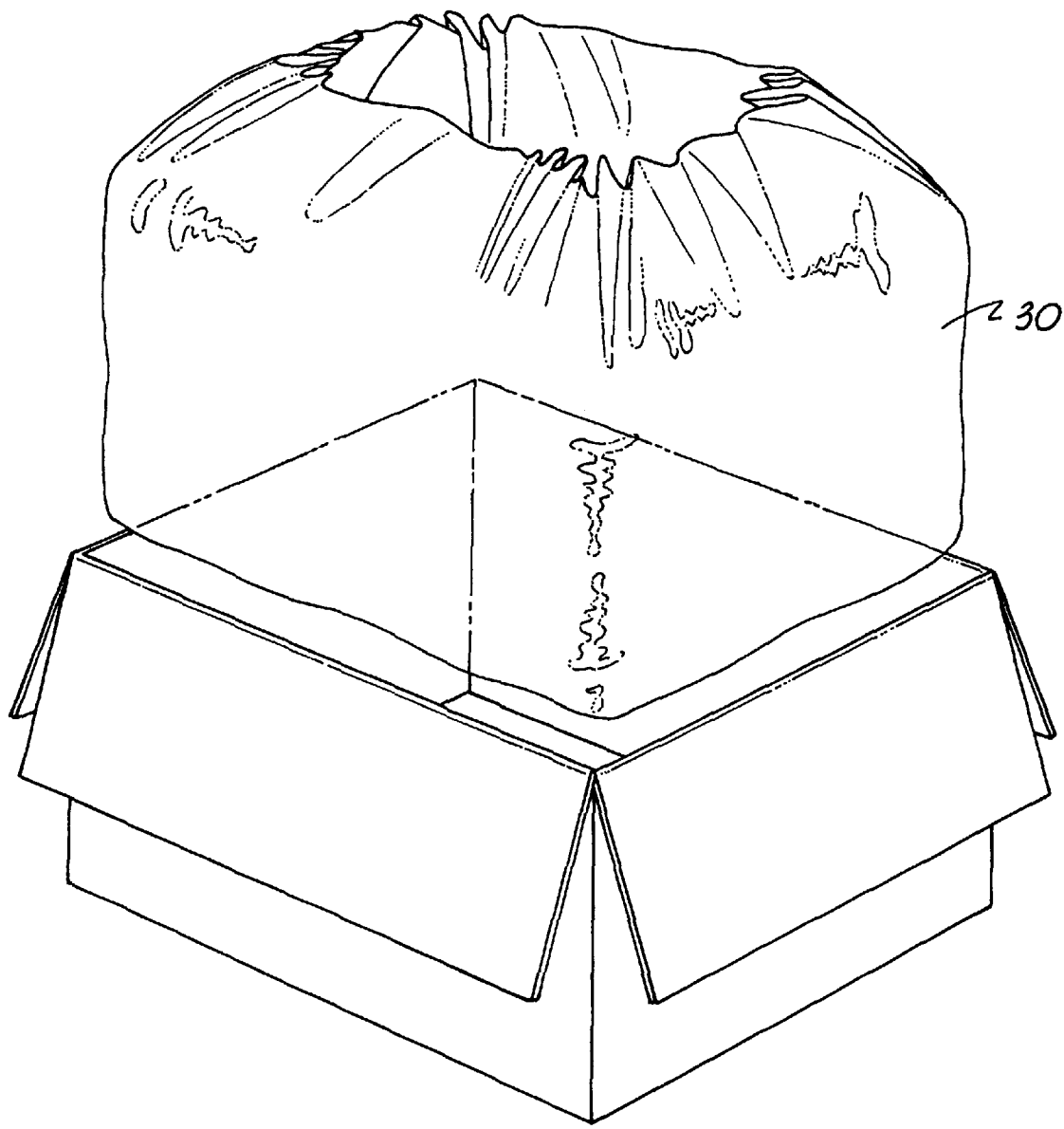
FIG. 3 is a perspective view of a box liner made in accordance with the present invention.

Referring to FIG. 3, a liner 30 is shown made from film 20 in FIG. 2. Liner 30 also may be used for a number of applications. For instance, liner 30 can be used for the transportation and shipment of cut flowers. As with produce, cut flowers typically have a short shelf life and are prone to attack by microorganisms. Liner 30 could be used to cover and protect any such plants.

Other uses for liner 30 include holding infectious wastes. With the increasing number of infectious agents, such as HIV and Hepatitis virus, transmitted via contact with blood and other bodily fluids, wastes generated by hospitals, clinics, and laboratories have created disposal concerns. Liner 30 could be used to contain such wastes and control pathogens which may leak or spill onto the outer surface of the bag and infect handlers. Liner 30 may also be used for a cat litter box liner. Preferably, the product contains capsicum in an amount of approximately 5 ppm, grapefruit seed extract in an amount of approximately 25,000 ppm and BIOCIDIN or Lemon Grass Oil in an amount of approximately 5,000 ppm. The product could be used without threat to any pets.

Figure 4:
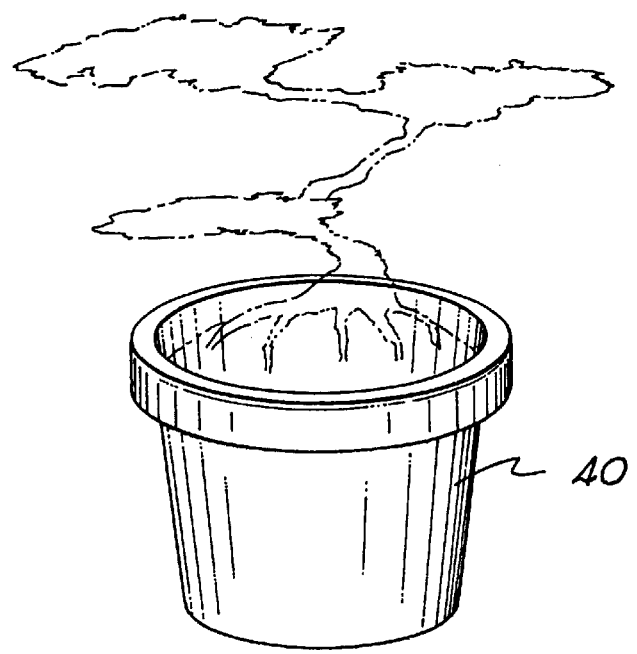
FIG. 4 is a perspective view of a pot for a plant in accordance with the present invention.
Figure 5:
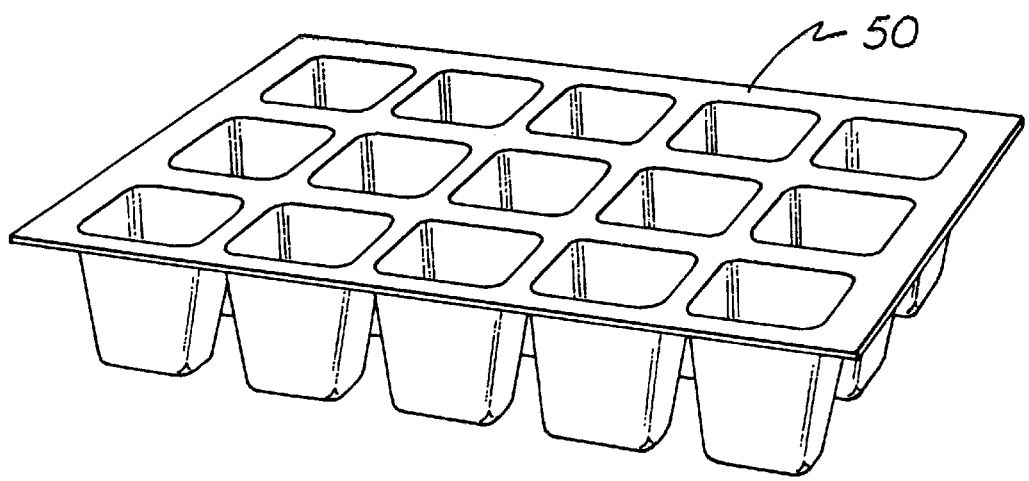
FIG. 5 is a tray for plants for germination of seeds made in accordance with the present invention.

FIGS. 4 and 5 represent further articles made from the composition of the present invention. Illustrated in the figures is a floral bucket 40 and a plant starter tray 50. Antimicrobial agents contained within the products protect the plants and seedlings from microbial attack. Further, the antimicrobial agents destroy or inhibit any harmful microorganisms found within the soil or any soil additives. Vitamin E may be used both as an antimicrobial and as a migration controller to retard the release of other biocides extruded in the polymeric material. Preferably, floral bucket 40 includes about 0.5 ppm capsicum, 30,000 ppm grapefruit seed extract, and approximately 15,000 ppm BIOCIDIN or Lemon Grass Oil. Plant starter tray 60 would preferably contain 0.5 ppm capsicum, 30,000 ppm grapefruit seed extract, and approximately 20,000 ppm BIOCIDIN or Lemon Grass Oil. Of course, these amounts vary depending upon the type of plant grown.

The composition of the present invention can also be extruded into particles and granules of any particular size. The particles or granules can be used in agricultural applications for nursery potting soil or for golf course greens and grass. In one particular application, the granules include grapefruit seed extract in an amount of approximately 25,000 ppm, trichloromelamine and citric acid in an amount of approximately 10,000 ppm (each), and BIOCIDIN or Lemon Grass Oil in an amount of approximately 15,000 ppm.

The present invention may be better understood by reference to the following example.

EXAMPLE

The following study was conducted to determine bacterial counts obtained from chicken stored in antimicrobial films, as compared to that wrapped in commercial plastic packaging film.

Chicken parts were packaged in film at a commercial facility and kept at temperatures below 38° F. prior to testing. Two types of antimicrobial films were tested. Mag 1 was made by extruding capsicum into PVC 60 gauge film at 1.7 ppm plus Vitamin E at 2,000 ppm. Mag 2 was made by extruding zinc pyrithione at a concentration of about 1,000 ppm plus Vitamin E at a concentration of about 2,000 ppm. Control film consisted of commercial plastic wrap. From each package, triplicate samples were collected at varying intervals (days 0, 3, 6, 9, 12, 14 and 18), plated onto appropriate media, and bacterial counts determined. Counts for days 0, 3, 9, and 12 were obtained by plating samples from a 100 ml rinse obtained from the chicken. Day 18 counts were determined from 25 g pieces of chicken, excised and diluted 1:10 with BPB before culture, while day 14 counts were determined for both rinse and excision samples.

The study showed that there were no significant differences in bacterial counts between experimental samples wrapped in antimicrobial wrap and controls wrapped in commercial film, when cultures were obtained from rinse samples. These results indicate that the antimicrobial film must be in close contact with the material, in order to inhibit microorganisms. Therefore, Day 14 samples were cultured from a 25 g excision piece of chicken, as well as from the 100 ml rinse. The samples cultured at Day 18 were obtained solely from the excision method.

Table 1 shows Day 14 and Day 18 bacterial counts, obtained from 25 g chicken samples wrapped in control film, as compared to samples from chicken wrapped in two concentrations of antimicrobial film, Mag 1 and Mag 2.

Mag 2 showed a significant reduction as compared to controls, at all time points with one exception. The Day 18 sample from chicken wrapped in the Mag 2 film did not show a reduction in coliform colonies.

The results of this study show that wrapping chicken in an antimicrobial film, such as Mag 1 (containing 1.7 ppm capsicum plus 2,000 ppm Vitamin E in a 60 gauge PVC polymer) or Mag 2 (containing zinc pyrithione plus 2,000 ppm Vitamin E in a 60 gauge PVC polymer), can significantly inhibit associated bacteria.

It should be understood that the present invention is not limited to the specific compositions or methods described herein and that any composition having a formula or method steps equivalent to those described falls within the scope of the present invention. Preparation routes of the composition and method steps for controlling the release of antimicrobial agents are merely exemplary so as to enable one of ordinary skill in the art to make the composition and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the following claims.

What is claimed is:

1. A polymeric material containing antimicrobial agents for inhibiting the growth of microorganisms in close proximity to said polymeric material, said polymeric material comprising:

TABLE 1

BACTERIAL COUNTS FROM 25 g EXCISION SAMPLES

|  | TPC 35° C. | TPC 20° C. | TPC 5° C. | LAC 30° C. | LAC 20° C. | LAC 5° C. | E. coli | Coliform |
|---|---|---|---|---|---|---|---|---|
| Control Day 14 | 9.31E + 05 | 3.40E + 06 | 4.43E + 06 | 1.44E + 04 | 1.13E + 04 | 1.00E + 01 | 1.00E + 01 | 4.67E + 01 |
| Mag 1 Day 14 | 3.72E + 05 | 3.35E + 06 | 2.18E + 06 | 2.60E + 03 | 2.20E + 03 | 1.00E + 01 | 1.00E + 01 | 1.00E + 01 |
| Mag 2 Day 14 | 5.37E + 04 | 5.53E + 05 | 1.01E + 06 | 2.93E + 03 | 2.84E + 03 | 1.00E + 01 | 1.00E + 01 | 1.00E + 01 |
| Control Day 18 | 3.64E + 07 | 6.67E + 07 | 4.59E + 07 | 3.38E + 05 | 4.00E + 05 | 1.00E + 01 | 1.00E + 02 | 2.00E + 02 |
| Mag 1 Day 18 | 5.80E + 05 | 3.87E + 06 | 2.78E + 07 | 3.13E + 03 | 3.33E + 03 | 1.00E + 01 | 1.00E + 02 | 1.00E + 02 |
| Mag 2 Day 18 | 2.98E + 07 | 3.61E + 07 | 4.93E + 06 | 1.09E + 05 | 1.42E + 03 | 1.00E + 01 | 1.00E + 02 | 1.03E + 03 |

Mag 1 = 1.7 ppm capscium plus 2,000 ppm Vitamin E;
Mag 2 = 2500 ppm pyrithione plus 2000 ppm Vitamin E;
Control = Commercial Plastic Wrap;
TPC = total plate count;
LAC = Lactic acid bacteria count;
E. coli = E. coli colonies;
Coliform = Coliform colonies Results: Both Day 14 and Day 18 total plate counts (TPC) show a significant decrease in samples from Mag 1 or Mag 2 film, as compared to controls, at the majority of the time points tested. Only the Day 14 Mag 1 sample, incubated at 20° C., showed no significant TPC reduction as compared to the control count.

Similar results were seen when comparing lactic acid bacteria counts (LAC) between experimental samples (Mag 1 or Mag 2 film) and controls. A significant reduction in bacteria numbers was seen in all experimental groups, as compared to controls, except samples incubated at 5° C.

The incubation of samples for *E. coli* counts did not show any differences between the number of colonies isolated from control plates, as compared to experimental samples. However, the total number of *E. coli* colonies cultured was too low to permit the drawing of any meaningful conclusions.

At both Day 14 and Day 18, the number of coliform bacteria cultured from chicken samples wrapped in Mag 1 or a polymeric article, said polymeric article being made from a polymer selected from the group consisting of silicones, polystyrenes, polyacrylates, polyurethanes, polyalkylenes, polyolefins, polyvinyls, synthetic rubbers, latex, N-propylsilicate and mixtures thereof;

a release agent; and at least one biocide dispersed within said polymeric article, said biocide being present in said polymeric article in an amount sufficient to inhibit the growth of microorganisms that come in contact with said polymeric article, said release agent being present to control release of at least one biocide from said polymeric article, said biocide comprising a photochemical derived from a naturally occurring source, wherein said photochemical is selected from the group consisting of capsicum, grapefruit seed extract, lemon grass oil, tea tree oil, citric acid, and mixtures thereof.

2. A polymeric article as defined in claim 1, wherein said release agent comprises said biocide.

3. A polymeric material as defined in claim 1, wherein said release agent comprises citric acid.

4. A polymeric material as defined in claim 1, wherein said release absent comprises Vitamin E.

5. A polymeric material as defined in claim 1, wherein said biocide is contained in a liquid carrier.

6. A polymeric material as defined in claim 5, wherein said liquid carrier comprises an epoxidized vegetable oil or propylene glycol.

7. A polymeric material as defined in claim 1, wherein said at least one biocide is present in said polymeric substrate in an amount up to about 100,000 ppm.

8. A polymeric material as defined in claim 1, wherein said at least one biocide is present within said polymeric substrate in an amount up to about 50,000 ppm.

9. A polymeric material as defined in claim 1, wherein said polymeric article comprises a plastic film.

10. A polymeric material as defined in claim 1, wherein said polymeric article comprises a plastic container.

11. A polymeric material as defined in claim 9, wherein said plastic film comprises polyethylene.

12. A polymeric material as defined in claim 1, wherein said photochemical is capsicum.

13. A polymeric material as defined in claim 1, wherein said photochemical is grapefruit seed extract.

14. A polymeric material as defined in claim 13, wherein said polymeric article is tubing comprising latex.

15. A polymeric material as defined in claim 1, wherein said photochemical is tea tree oil.

16. A polymeric material as defined in claim 15, wherein said polymeric article is tubing comprising latex.

17. A polymeric article as defined in claim 1, wherein said photochemical is citric acid.

* * * * *

UNITED STATES PATENT AND TRADEMARK OFFICE
CERTIFICATE OF CORRECTION

PATENT NO. : 5,906,825 Page 1 of 1
DATED : May 25, 1999
INVENTOR(S) : Samuel G. Seabrook, Jr. and William E. Craver, III It is certified that error appears in the above-identified patent and that said Letters Patent is hereby corrected as shown below:

Column 20,
Lines 6, 8 and 12, "photochemical" should read -- phytochemical --.

Signed and Sealed this

Twenty-first Day of June, 2005

JON W. DUDAS
*Director of the United States Patent and Trademark Office*